United States Patent [19]
Fukunaga et al.

[11] Patent Number: 6,025,362
[45] Date of Patent: Feb. 15, 2000

[54] USES OF XANTHINE COMPOUNDS

[76] Inventors: Atsuo F. Fukunaga, 5411 Littlebow Rd., Rancho Palos Verdes, Calif. 90275; Alex S. Fukunaga, 1030 El Monte Ave., Mountain View, Calif. 94040

[21] Appl. No.: 09/143,882

[22] Filed: Aug. 31, 1998

[51] Int. Cl.[7] ................................................. A61K 31/52
[52] U.S. Cl. ........................................................ 514/263
[58] Field of Search .................................... 514/262, 263

[56] References Cited

U.S. PATENT DOCUMENTS

| | | | |
|---|---|---|---|
| 5,677,290 | 10/1997 | Fukunaga | 514/46 |
| 5,679,650 | 10/1997 | Fukunaga et al. | 514/46 |
| 5,696,124 | 12/1997 | Kufner-Muhl et al. | 514/263 |
| 5,734,052 | 3/1998 | Peet et al. | 544/273 |

OTHER PUBLICATIONS

*Merck Index*, 12th Ed., Merck & Co., Inc., Whitehouse Station, NJ, (1996), p. 487.

Rodrigo, et al., "Aminophylline Fails To Reverse Conscious Sedation With Midazolam in Dentistry," *Anesth. Progress*, May/Jun. (1986), pp. 152–154.

Aldrete, et al., "A Postanesthetic Recovery Score," *Anesth Analg*, vol. 49 (1970), pp. 924–933.

Ramsay, et al., "Controlled Sedation with Alphaxalone–Alphadolone," *Br Med J.*, vol. 2 (1974), pp. 656–659.

Bruns, "Adenosine Antagonism By Purines, Pteridines, And Benzopteridines In Human Fibroblasts," *Biochem Pharmacol* vol. 30 (1981), pp. 325–333.

Fukunaga, et al., "Assessment of Various Endpoints In Anesthesia During Noxious Stimulation In The Animal Model Using Inhalation And Intravenous Anesthetic And Analgesic Agents," *Anesthesiology*, vol. 87 (1997) A287.

Arvidsson et al., "Aminophylline Antagonizes Diazepam Sedation," *Lancet*, vol. 2 (1982) p. 1467.

Maroof et al., "Aminophylline Expedites Recovery From Ketamine Anesthesia," *Anesth Analg*, vol. 86 (1998) S480.

Batrak et al., Zh. Vyssh. Nervn. Deyat. im. I. P. Pavlova, 25(3), 541–544 (abstract), 1975.

*Primary Examiner*—Phyllis G. Spivack
*Attorney, Agent, or Firm*—Daniel B. Schein, Esq.

[57] ABSTRACT

Xanthine compounds are utilized to accelerate anesthetic recovery from the effects of certain compounds as propofol, etomidate, barbiturates, opioids, isoflurane, enflurane, halothane, desflurane, sevoflurane and/or nitrous oxide. In a preferred embodiment, dialkyl substituted xanthines are utilized.

16 Claims, 1 Drawing Sheet

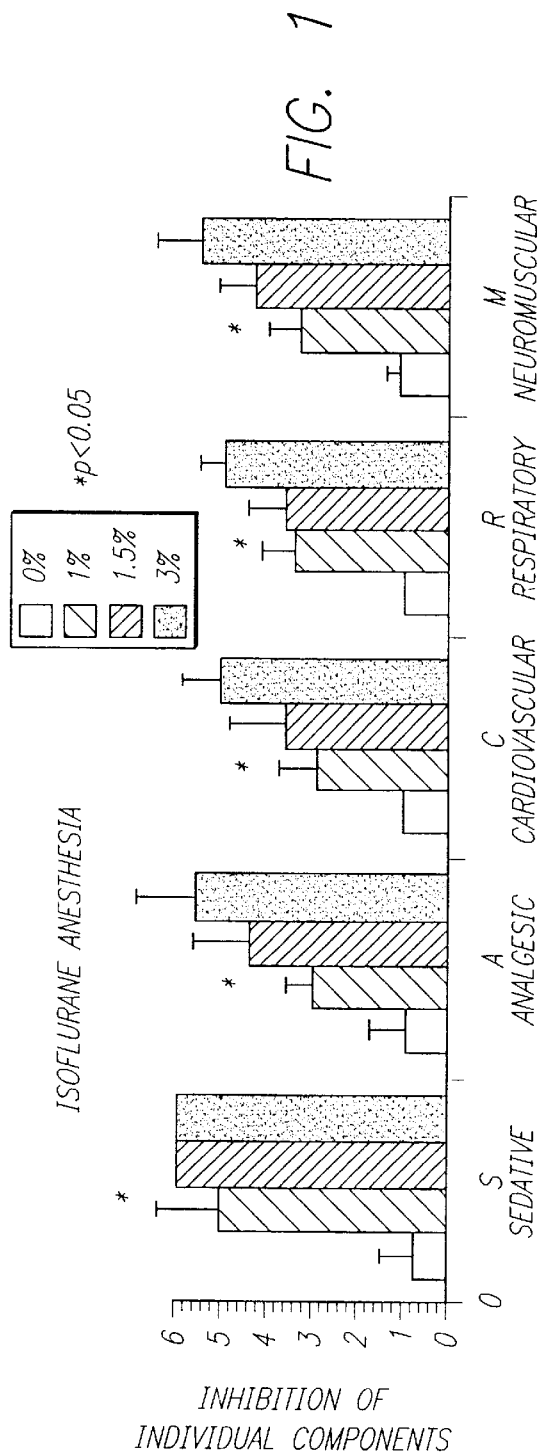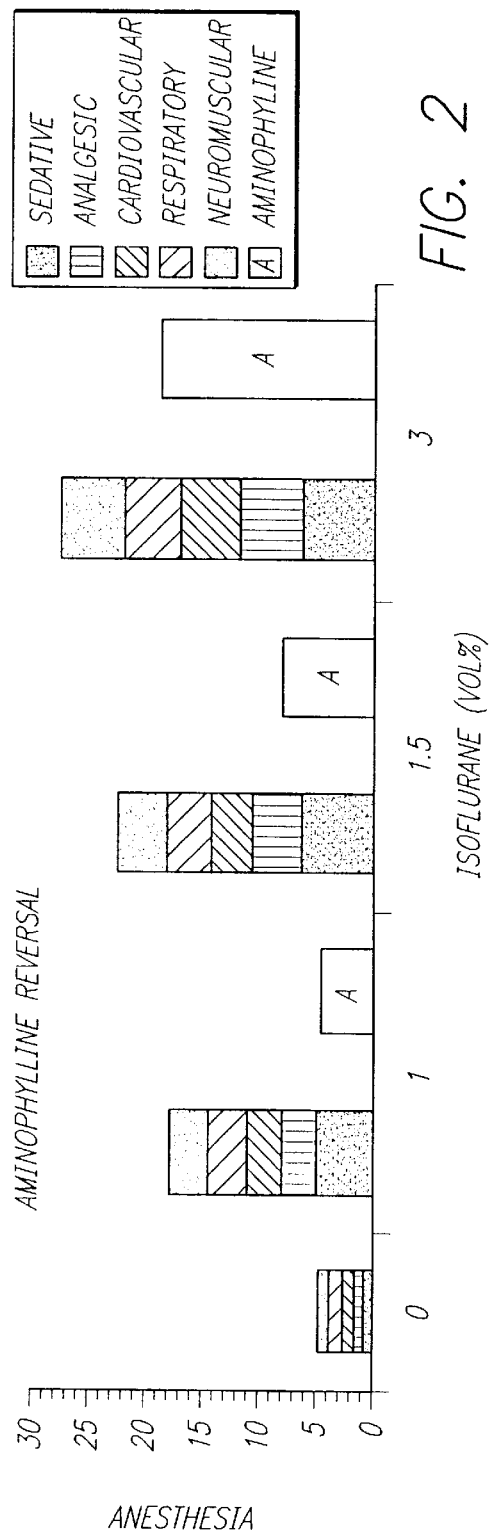

USES OF XANTHINE COMPOUNDS

FIELD OF THE INVENTION

The present invention is directed to the use of xanthine compounds in medicine, and more particularly to the use of xanthine compounds to counteract the effects of certain classes of drugs.

BACKGROUND OF THE INVENTION

Xanthine has the general structure:

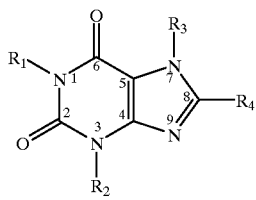

wherein $R_1$, $R_2$, $R_3$, & $R_4$ are each H. Xanthine compounds are referred to herein as compounds wherein $R_1$, $R_2$, $R_3$, & $R_4$ are independently selected from the group of moieties consisting of a hydrogen, an alkyl, an alkenyl, an alkynyl, an alkoxy, an amino, an aryl, a cycloalkyl, a hydroxy, a halogen, and a nitro.

Well known xanthine compounds include theophylline (1,3-dimethyl xanthine; i.e., $R_1$ and $R_2$ are $CH_3$ and $R_3$ and $R_4$ are H in the general structure above), theobromine (3,7-dimethyl xanthine; i.e., $R_2$ and $R_3$ are $CH_3$ and $R_1$ and $R_4$ are H in the general structure above). Of particular interest to the present invention, are compounds wherein at least two of $R_1$, $R_2$, and $R_3$ are each independently a $C_1$–$C_4$ lower alkyl, including but not limited to the dimethyl and trimethyl substituted forms, such as 1,7-dimethyl xanthine, and 1,3,7-trimethyl xanthine, as well as 8-substituted compounds (e.g., 1,3-dimethyl, 8-phenyl xanthine). For example, xanthine compounds include theophylline and derivatives thereof, including pharmaceutically acceptable salts thereof. Since the aqueous solubility of xanthine compounds tends to be low, reference to xanthine and xanthine compounds referred to herein also includes water soluble derivatives and complexes thereof. For example, the term theophylline includes the water soluble compound aminophylline, which is formed by the combination of theophylline with ethylenediamine (2:1).

The present invention arose from the need to find drugs which will counteract the intended effects and/or side-effects of other useful drugs. For the purpose of facilitating the description of the present invention, it is important to appreciate that, despite advances in understanding the molecular basis of drug actions, such as drug-receptor interactions, the mechanisms of action of many drugs that are presently used is not clearly understood. Thus, the difficulty in characterizing the biochemical actions of the drugs in complex physiological systems makes it extremely difficult to develop pharmacologic antagonists to counteract their intended effects and/or side-effects. Furthermore, when drugs with similar pharmacological effects are administered concurrently, an additive or synergistic response is frequently seen, thereby compounding the problem in antagonizing the effects of the administered drugs. Hence, despite the long felt and great need to develop drugs to counteract the intended effects and/or undesired side-effects of drugs administered for useful purposes, there are few antagonists which enable a physician to achieve a desired effect with one drug, and to reverse an intended effect and/or undesired side effects with another drug. This need is particularly strong in the field of anesthesia.

For example, opioids are very useful drugs for analgesia and for producing anesthesia, but unfortunately can cause serious side effects including respiratory depression and arrest, which may cause hypoxia and death at high dosages. The drug naloxone has been found to counteract the respiratory depression effects of opioids, but also reverses the desired beneficial effects, namely analgesia. It is believed that naloxone competitively binds to opioid receptors.

Because of the inherent toxic and dangerous actions that certain drugs have and their low therapeutic ratio (toxic dose/therapeutic dose), there is a need for an antagonist drug to reverse or antagonize the dangerous and/or undesired effects of an administered drug, shorten the duration of the effects of an administered drug, and/or attenuate some or all of the effects of an administered drug. This is particularly true for drugs used in producing anesthesia for surgery or other purposes, wherein numerous drugs are concurrently administered to induce and/or maintain the variety of effects constituting anesthesia.

General anesthesia usually includes analgesia, hypnosis (sedation, amnesia, loss of consciousness), inhibition of sensory and autonomic reflexes, and, in many cases, skeletal muscle relaxation. An ideal combination of drugs for anesthesia would induce anesthesia smoothly and rapidly, and permit rapid recovery as soon as the administration of the drugs is ceased. Some of the drugs used in anesthesia have specific antagonists. Naloxone is used to antagonize opioid effects, flumazenil is used to antagonize benzodiazepines and neostigmine antagonizes the effects of muscle relaxants. However, there are no known antagonists to reverse the anesthetic effects of the inhaled anesthetics, or certain other classes of drugs useful in producing anesthesia, including propofol, barbiturates, etomidate, and certain purine compounds recently discovered to be useful in producing anesthesia. Thus, while naloxone reverses the effects of opioids, flumazenil reverses the effects of benzodiazepines and neostigmine reverses the effects of certain muscle relaxants, these drugs do not work to reverse the effects of other classes of drugs concurrently used in producing effects required for anesthesia, including surgical anesthesia. This illustrates the unpredictable nature of anesthetic drugs, and the difficulty of finding antagonist drugs, which can be safely used to counteract the effects of the various drugs used in the practice of modern anesthesia.

A major concern of anesthesiology is recovery from anesthesia. Most drugs used in anesthesia acutely depress the central nervous system (CNS) and inhibit protective reflexes (i.e., disrupt homeostasis and inhibit physiological functions required to live). In addition, the drugs that produce anesthesia also produce potent autonomic nervous system (ANS) side effects. The vital signs that an anesthesiologist usually monitors continuously during anesthesia often reflects ANS function and homeostasis. The use of potent anesthetics modifies the actions of a patient's body regulating functions, therefore, it is important to restore those physiological functions as soon as the need for anesthesia ends. Ideally, anesthesia is a totally reversible process, and most of the anesthetic agents currently used are relatively short-acting and safe. However, failure to promptly recover from anesthesia is always a major concern.

In modern anesthesia practice, the anesthetist is faced with challenges to the health of the patient due to the potent drugs used during the course of anesthesia. Thus, there is an urgent need for agents that will ensure that the side effects or toxicity of the potent drugs used to produce anesthesia are quickly counteracted at the end of the anesthetic procedure, and/or that the effects are shortened after surgery and anesthesia. Thus, it is desirable that the time for initial awakening, orientation and return of normal psychomotor performance be as short as possible after anesthesia. Most importantly, the quickest possible return of the patient's homeostatic mechanisms is a primary goal following any anesthetic procedure.

Anesthetics produce significant changes in mental function, which persist beyond the period of the anesthetic administration and the immediate postoperative period. Following prolonged anesthesia, subjects exhibit decreased intellectual function and increased incidence of subjective symptoms. Furthermore, it has been recognized in general that anesthetics, particularly the inhaled anesthetics and propofol, produce significant cardio-respiratory depression, which is dose-related. Therefore, there is a need for a drug and/or drugs to counteract and or shorten the CNS side effects of drugs used to produce anesthesia, including effects which persist postoperatively, such as obliviousness, inhibition, depression, and/or limitation of cognitive functions. The need also exists for a method to improve the recovery of psychomotor function after anesthesia is ended. A need exists for shorter recovery times, which could result in less health care costs by reducing the requirement for recovery room nurses, and special monitoring in the post-anesthesia care unit. A further need exists for a general method to hasten recovery of respiratory and cardiovascular functions after anesthesia.

BRIEF DESCRIPTION OF THE INVENTION

The present invention provides a method for reducing the period of anesthesia recovery after administration of anesthesia-producing drugs is ended, comprising administration of a xanthine compound. In a preferred embodiment, a pharmaceutically acceptable, water soluble theophylline compound is administered to a patient to accelerate recovery from anesthesia. A preferred water soluble xanthine compound useful for performing the present invention is aminophylline. The method of the present invention shortens the time required for substantially complete recovery of psychomotor functions. Furthermore, with respect to respiratory function, the respiratory depression caused by the anesthetic drugs, or caused by the interaction of the various drugs used during anesthesia, are counteracted after anesthesia. For example, the time for the return of spontaneous (normal) respiration without the need of artificial ventilation is significantly shortened.

In a preferred, non-limiting embodiment, aminophylline is administered in an amount effective both to restore the psychomotor functions as well as the cardiorespiratory functions at a level substantially equal to that of pre-anesthetic levels. Thus, in the present invention, normalization, and the rates of recovery of psychomotor, cardiac and respiratory functions are enhanced following administration of aminophylline.

Preferred embodiments of the present invention include the use of a xanthine compound having the general structure:

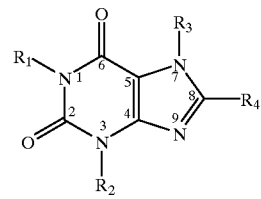

for reducing the recovery time from anesthesia, wherein anesthesia was produced using at least one compound selected from the group consisting of an inhaled anesthetic, propofol, an etomidate, a barbiturate, an opioid, and a purine compound, wherein $R_1$, $R_2$, $R_3$, & $R_4$ are independently selected from the group of moieties consisting of a hydrogen, an alkyl, an alkenyl, an alkynyl, an alkoxy, an amino, an aryl, a cycloalkyl, a hydroxy, a halogen, and a nitro.

Non-limiting examples of preferred inhaled anesthetics used to produce anesthesia are selected from the group consisting of isoflurane, enflurane, halothane, desflurane, sevoflurane, and nitrous oxide. A non-limiting example of a preferred etomidate is AMIDATE® (available from Abbott Laboratories). A non-limiting example of a preferred barbiturate is methohexital sodium, BREVITAL SODIUM® (available from Jones Medical Industries). Preferred purine compounds and/or compositions useful for producing anesthesia are adenosine, adenosine monophosphate, adenosine diphosphate, and adenosine triphosphate, as well as combinations thereof with a catecholamine. A non-limiting example of a preferred propofol (alkyl phenol) is DIPRIVAN® (available from Zeneca Pharmaceuticals). A non-limiting example of a preferred benzodiazepine is midazolam HCl, VERSED® (available from Roche Laboratories).

DESCRIPTION OF THE FIGURES

FIG. 1 includes five graphs illustrating five effects of isoflurane anesthesia. Graph 1 illustrates how increasing doses of isoflurane (0%, 1%, 1.5%, and 3%, each dosage represented by a corresponding vertical bar) have an increased sedative (sedative/hypnotic) effect, up to a maximum sedative effect. An Inhibition End-point score of 0 means a minimum sedative effect and a score of 6 means maximum effect. Likewise, Graphs 2, 3, 4 and 5, respectively, illustrate the effects of increasing doses of isoflurane on analgesic, neuromuscular, cardiovascular, and respiratory parameters.

FIG. 2 illustrates aminophylline's inhibition of five effects of isoflurane anesthesia, and the Fukunaga criteria for anesthesia recovery. The vertical axis provides a combined anesthesia score. The horizontal axis provides the concentration of isoflurane administered. The seven vertical bars represent the stacked or combined scores for the sedative, analgesic, neuromuscular, cardiovascular, and respiratory parameters measured. Bars having the letter A appearing vertically thereover or therein represent scores after administration of aminophylline (30 mg/kg), injected into a peripheral vein over five minutes. Moving from left to right, the first bar represents the baseline score when no isoflurane or aminophylline is provided. The second bar represents the score from administration of 1% (by volume) isoflurane, and the third bar represents the score following administration of aminophylline to a subject being administered 1% isoflurane. The 4th and 5th bars, and 6th and 7th bars, are paired in the same fashion, except for provision of 1.5% and 3% isoflurane, respectively. Note that aminophylline significantly diminished the effects of isoflurane despite the fact that the rabbit is being subjected to isoflurane administration.

DETAILED DESCRIPTION OF PREFERRED EMBODIMENTS

Methylxanthines, such as theophylline and theobromine, share several pharmacological actions of therapeutic interest. They relax smooth muscle, notably bronchial muscle, stimulate the central nervous system (CNS), stimulate cardiac muscle, and act on the kidney as a diuretic. It is known that methylxanthines inhibit cyclic nucleotide phosphodiesterases and antagonize receptor-mediated actions of adenosine, the two best-characterized cellular actions of the methylxanthines. Theophylline has been used as a therapeutic agent in the treatment of asthma along with inhaled sympathomimetic agents and inhaled antiinflammatory agents. The theophylline preparation most commonly used for therapeutic purposes is aminophylline. Aminophylline is known as a bronchodilator, and has been shown to relieve airflow obstruction in acute asthma. Aminophylline has been the mainstay in the treatment of asthma and bronchospasm for almost a century because of its strong $beta^2$ mimetic effect.

The use of aminophylline during the course of anesthesia has been limited to the treatment of asthmatic patients, and for the purpose of producing bronchodilation. Aminophylline is also believed to be a diazepam and ketamine antagonist. However, its use to counteract or antagonize the effects of other classes of drugs used in anesthesia, and/or for other purposes has not been pursued, but rather discouraged: "Caution: Acute poisoning . . . May result in cardiovascular and respiratory collapse, shock, cyanosis and death." *Merck Index*, (Merck & Co., Inc., Whitehouse Station, N.J., 12th Ed. 1996), p. 81, citing *Clinical Toxicology of Commercial Products*, R. R. Gosselin el al., Eds. (Williams & Wilkins, Baltimore, 4th Ed., 1976), Section III, pp. 16–20. Other documents disclosing the effects of xanthine compounds include U.S. Pat. Nos. 5,696,124 and 5,734,052. Also see Goodmann & Gilman's, *The Pharmacological Basis of Therapeutics. Ninth edition* (Edited by J G Hardman, L E Limbird, P B Molinoff, R W Ruddon, A Goodman Gilman. New York, McGraw-Hill, 1996); and *Basic & Clinical Pharmacology. Sixth edition* (Edited by B G Katzung, Norwalk, Conn., Appleton & Lange, 1995). All documents referred to in this specification are incorporated by reference as if reproduced in full below.

Aminophylline use has been further discouraged since it is known to interact with volatile anesthetics. It is known that catecholamines influence the accumulation of cAMP by activating adenyl cyclase. Increased catecholamine levels, combined with the xanthines, may lead to synergistic adrenergic activity by increasing production and reducing breakdown of cAMP. Cardiac dysrhythmias are common in such circumstances and are further potentiated during general anesthesia with halothane. Serious cardiac dysrhythmias and cardiac arrest have been reported with the combination of aminophylline and halothane, when it has not been carefully controlled. Therefore, it is believed that the use of aminophylline for any other purpose during the course of anesthesia would be avoided and discouraged. Hence, it is very surprising and unexpected that aminophylline, a xanthine, reversed the undesired effects including respiratory depression, without exacerbating the postoperative pain.

The present invention arose from the surprising discovery that asthmatic patients treated with a xanthine compound after anesthesia recovered from anesthesia much faster, despite being deeply anesthetized for relatively longer periods of time than non-asthmatic patients. The administration of a xanthine compound during or immediately after anesthesia counteracted the side effects of the anesthetics, namely, respiratory depression and cardiovascular depression, and shortened the cognitive and psychomotor inhibitory actions produced by the anesthetics. However, corroboration of such an effect of a xanthine (e.g., theophylline, 8-phenyl theophylline, 8-(p-sulfophenyl) theophylline, etc.) required careful and systematic investigation, which included devising an experimental methodology before being able to test it in the clinical setting.

In a preferred embodiment, the present method comprises the administration of a methylxanthine to a mammal during, and/or after, anesthesia to reduce anesthetic effects. In another embodiment, aminophylline is administered to a patient to accelerate recovery from anesthesia, such as anesthesia produced by anesthetic gases. In another embodiment, aminophylline is administered to a mammal after propofol anesthesia to reverse the effects of propofol.

The rate of administration and the total dose of a xanthine compound can be varied over a wide range, and will be dependent on a number of variables, including the type of anesthetic(s) used, the extent of the anesthetic depression effect, the characteristics and conditions of the subject, etc., all of which a medical practitioner will readily understand. In a preferred embodiment, aminophylline, at a dosage of 5–6 mg/kg, is administered slowly to a patient via intravenous injection during anesthesia, and, at the end of administration of the anesthetic drugs, a subsequent lower dosage of aminophylline is infused; this method has been shown to be effective in reducing anesthetic recovery time. The appropriate dose for optimal anesthetic recovery in a given human subject can be readily established by one familiar with anesthesiology without undue experimentation using standard dosage determining techniques.

EVALUATING ANESTHESIA RECOVERY

There are standard tests for evaluating the degree or level of postanesthesia recovery, including the sedative-hypnotic effect. For example, the well-known Aldrete score uses a scale of 0 to 10 to determine the postanesthetic recovery level of a patient, with a score of 0 indicating the worst condition (indicating that maximal residual anesthetic effect was present), and a score of 10 indicating a patient in the best possible condition (i.e., no residual anesthetic effect, see: Aldrete J A, Kroulik D: "A postanesthetic recovery score," *Anesth Analg*, 1970;49:924–933). In clinical practice, a patient with an Aldrete score below 8 is generally not recommended for discharge (i.e., the patient is kept for observation in the recovery room). As postanesthetic recovery progresses and the status of the patient achieves a score above 8, the patient is ready to be discharged from the recovery room to the ward. The Ramsay score uses a scale of 0 to 6 to determine the level of sedation, with a score of 0 indicating no sedative effect, and a score of 6 indicating maximum sedative effect (see: Ramsay M. A. E. et al, "Controlled Sedation With Alphaxalone-alphadolone," *Br Med J*, 1974; 2:656–659).

The Fukunaga criteria for evaluating anesthetic effects assigns scores for five critical end-points (parameters or variables) measured, which are continuously monitored during anesthesia and postanesthesia. The combined scores of these parameters (Fukunaga score) can be used for evaluating recovery from anesthesia (i.e., reversal of effects produced by an anesthetic agent). Sedative, analgesic, cardiovascular, respiratory, and neuromuscular parameters are each given a score between 0 and 6. For example, the sedative parameter score is analogous to the Ramsay score mentioned above. The cardiovascular (blood pressure, or "BP," and heart rate, or "HR") and respiratory (respiratory rate and $PCO_2$) end-points provide scores of up to 3 for each specific variable resulting in a score of up to 6 for each end-point respectively. The combined scores provide a Fukunaga score between 0 and 30. By comparing the Fukunaga scores at various times after a desired depth or level of anesthesia is produced and after administration of the drugs producing anesthesia stops, the rate of unassisted anesthetic recovery can be determined. The rate of anesthetic recovery from anesthesia for subjects administered at least one xanthine compound can be evaluated with Fukunaga scores by comparing the rate of anesthetic recovery following administration of a drug with the rate of anesthetic recovery without the drug (i.e., unassisted anesthetic recovery). Using Fukunaga scores to determine anesthetic recovery rates permits a more accurate determination of the effect of a xanthine compound, and/or other drug, on the rate of anesthetic recovery.

Thus, as used herein, a drug is said to accelerate anesthetic recovery when, after termination of administration of anesthetic drugs to produce anesthesia, less time is required to achieve a second or lower Fukunaga score from a first or higher Fukunaga score relative to the time required when the drug is not administered. This relationship can be represented by the following equation:

$$\Delta AR = T_O - T_D,$$

where $\Delta AR$ represents the change in anesthetic recovery time, $T_O$ is the time to go from a first Fukunaga score ($F_1$) to a second Fukunaga score ($F_2$) when the particular xanthine compound is not administered, and $T_D$ is the time to go from the first Fukunaga score ($F_1$) to the second Fukunaga score ($F_2$) when the particular xanthine compound is administered. When $\Delta AR$ is greater than 0, the rate of anesthetic recovery is accelerated by the drug administered to the patient. When $\Delta AR$ is 0, the rate of anesthetic recovery is not affected by the drug administered. When $\Delta AR$ is less than 0, anesthetic recovery is adversely affected by the drug administered. Thus, xanthine compounds of the present invention, if administered during and/or after producing anesthesia in a patient, would accelerate the rate of anesthetic recovery, and would yield a $\Delta AR$ greater than 0.

Thus, in a preferred embodiment of the present invention, a pharmaceutically acceptable xanthine compound is administered to an anesthetized patient to accelerate anesthesia or postanesthesia recovery. In an alternative embodiment, a pharmaceutically acceptable xanthine compound is used to accelerate anesthesia or postanesthesia recovery in a patient in which anesthesia was produced with at least one compound selected from the group consisting of an inhaled anesthetic, propofol, an etomidate, a barbiturate, an opioid, a purine compound and a benzodiazepine compound.

The invention will be further understood and described by reference to the following examples:

EXAMPLE 1

AMINOPHYLLINE REVERSAL OF ISOFLURANE ANESTHETIC EFFECTS

Isoflurane is one of the most widely used inhaled anesthetics. Aminophylline is believed to be a competitive blocker of adenosine receptors at micromolar concentrations. See *Biochem Pharmacol,* 1981: 30:325–33. Whether aminophylline could antagonize isoflurane anesthetic effects was assessed by CNS and cardiovascular responses at three dosages.

Methods: After institutional approval, nine tracheotomized and intravascularly cannulated New Zealand White male rabbits (3 kg) were placed in a sling, which allowed free movement of the head and legs for behavioral observation. After complete recovery from anesthesia and the surgical preparation, the rabbit breathed 100% oxygen spontaneously. End-tidal isoflurane was increased in a stepwise fashion to 1, 1.5, and 3% concentrations. Each alveolar concentration was maintained constant for 30 min. Various end-points or parameters (effects produced by the anesthetic agent) were assessed. The end-points were: 1) sedative-hypnotic, 2) analgesic, 3) central neuromuscular relaxation, 4) cardiovascular, and 5) respiratory parameters. These parameters were tested in the animal model before and after aminophylline injection. For the animal model preparation, see *Anesthesiology,* 1997; 87:A287. Aminophylline reversal was tested as follows: During steady-state 1.5% anesthesia, a single dose of aminophylline (30 mg/kg) was slowly injected into a peripheral vein over 5 min. Repeated measurements were done in each incremental (3%) or decremental (1%) dose of isoflurane ("ISO"). Each parameter was given a score (0–6) for graphical description. Statistical analysis was done using analysis of variance ("ANOVA") and Kruskal-Wallis test, where $p<0.5$ was considered significant. Data are reported as mean±standard deviation ("SD").

Results and conclusion: With reference to FIG. 1, five graphs illustrate various end-points or effects produced by isoflurane anesthesia. Graph 1 in FIG. 1 (moving from left to right, the first bar on the left) illustrates how increasing doses of isoflurane have an increased sedative-hypnotic effect. A corresponding vertical bar is present for each dosage, 0%, 1%, 1.5%, and 3%. An Inhibition End-point score of 0 means less sedative effect is present, and a score of 6 means a maximum effect has been achieved. Likewise, Graphs 2, 3, 4 and 5 in FIG. 1 respectively illustrate the effect of increasing doses of isoflurane on analgesic, neuromuscular, cardiovascular, and respiratory end-points or parameters. Administration of increasing doses resulted in significant and dose-related inhibition of all of the end points studied.

With reference to FIG. 2, aminophylline's reversal (decrease) of the five end-points or effects measured in FIG. 1 is illustrated. The vertical axis provides a combined anesthesia score, or Fukunaga score, using the Fukunaga Criteria for Anesthesia Recovery (i.e., decrease of effects produced by the anesthetic drug or drugs administered). The horizontal axis provides the dosages of isoflurane administered. The seven vertical bars represent the stacked or combined scores (i.e., Fukunaga score) for the sedative, analgesic, neuromuscular, cardiovascular, and respiratory end-point measured. Bars having the letter "A" vertically therein represent scores after administration of aminophylline (30 mg/kg) injected into a peripheral vein over five minutes. Moving from left to right, the first bar represents the baseline Fukunaga score when no isoflurane or aminophylline is provided. The second bar represents the Fukunaga score from administration of 1% (by volume) isoflurane, and the third bar represents the Fukunaga score following administration of aminophylline to a subject being administered 1% isoflurane. The 4th and 5th bars, and 6th and 7th bars, are paired in the same fashion as the paired second and third bars, except that they represent results from use of 1.5% and 3% isoflurane, respectively.

Aminophylline abolished almost completely all of the effects produced by clinical doses of isoflurane (1 and 1.5%) but the reversal was partial at a higher (3%) dosage (FIG. 2). The present results suggest that aminophylline can be used as an antagonist of the various effects produced by isoflurane, and that there is a clinical implication regarding the reversal of isoflurane effects for the postanesthesia recovery in patients anesthetized with isoflurane. Thus, acceleration of anesthetic recovery has been demonstrated.

EXAMPLE 2

AMINOPHYLLINE REDUCES PROPOFOL ANESTHETIC EFFECTS

Propofol is an intravenous anesthetic agent, which is one of a series of alkyl phenols, and is chemically unrelated to barbiturate, steroid, imidazole, or eugenol agents. Propofol is presently the most widely used intravenous anesthetic. However, no antagonist of propofol is available. Therefore, we examined whether aminophylline could antagonize the effects produced by propofol to accelerate anesthetic recovery. As used herein, propofol (2,6-diisopropyl phenol) also refers to substituted phenol analogues and homologs thereof having substantially similar anesthetic properties, wherein such effects can be antagonized with a xanthine compound in accordance with the present invention.

Methods: After institutional approval, 9 tracheotomized and intravascularly cannulated New Zealand White male rabbits (3 kg) were placed in a sling, which allowed free movement of the head and legs for behavioral observation (the animal model preparation is described in Anesthesiology, 1997; 87:A287 and U.S. Pat. No. 5,677,290; also see U.S. Pat. No. 5,679,650 for other anesthetic compositions). After complete recovery from anesthesia and the surgical preparation, the rabbit breathed 100% oxygen spontaneously. Following an intravenous loading dose of propofol (2 mg/kg), an infusion dose of propofol was increased in a stepwise fashion to 200, 400 and 800 $\mu$g/kg/min, and each infusion dose was maintained constant for 30 minutes. Various effects (end-points or variables) produced by propofol were assessed. The following end-points were tested before and after administration of aminophylline: sedative-hypnotic response, analgesic, cardiovascular, respiratory, and central neuromuscular effects. Aminophylline reversal was tested as follows: During steady state anesthesia by propofol, aminophylline (30 mg) was slowly injected into a peripheral vein over 5 minutes. Repeated measurements were done for each incremental dose of propofol. The scoring system described above and in Example 1 was utilized for graphical description. Statistical analysis was done using ANOVA and Kruskal-Wallis test.

Results and Conclusion: Administration of propofol in increasing doses resulted in a dose-related and significant inhibition of all the variables measured. Aminophylline counteracted almost completely all of the effects produced by propofol administration even at the highest infusion rate of 800 $\mu$g/kg/min. The results suggest that aminophylline can be useful to reverse the effects produced by propofol and can accelerate anesthetic recovery in patients receiving propofol intraoperatively.

TABLE 1

PROPOFOL ANESTHESIA ANTAGONIZED BY AMINOPHYLLINE

| | | | ANESTHESIA SCORE | | |
| --- | --- | --- | --- | --- | --- |
| | | | | AMINOPHYLLINE (30 mg) | |
| ANESTHESIA End-Points | CONTROL | PROPOFOL (200 $\mu$g/kg/min) | A(1) (10 mg) | A(2) (10 mg) | A (3) (10 mg) |
| Sedation (0–6) | 0.7 | 2.9 | 0.6 | 0.3 | 0.2 |
| Analgesia (0–6) | 0.9 | 1.8 | 1.3 | 0.4 | 0.2 |
| Cardiovascular (0–6) | 1.0 | 1.4 | 0.1 | 0.0 | 0.4 |
| Respiratory (0–6) | 1.0 | 2.3 | 0.3 | 0.3 | 0.2 |
| Neuromuscular (0–6) | 1.1 | 1.7 | 1.1 | 0.6 | 0.4 |
| Total Score | 4.7 | 10.1 | 3.4 | 1.6 | 1.4 |

A:Aminophylline;
A(1):First dosage,
A(2):Second dosage,
A(3):Third dosage.
Note that during steady-state propofol anesthesia (200 $\mu$g/kg/min), IV aminophylline (30 mg), administered in divided doses of 10 mg each, reversed the propofol anesthesia in a dose dependent manner; Mean values(n = 9).

TABLE 2

INCREASING DOSES OF PROPOFOL ANESTHESIA ANTAGONIZED BY AMINOPHYLLINE

| PROPOFOL Infusion Doses | ANESTHESIA SCORE | |
| --- | --- | --- |
| ($\mu$g/kg/min) | Propofol Alone | Aminophylline (30 mg) |
| Awake P = O | 4.7* | 1.2 |
| P = 50 | 8.9 | — |
| P = 100 | 9.0 | — |
| P = 200 | 10.1 | 1.4 |
| P = 400 | 12.1 | 3.0 |
| P = 800 | 18.0 | 6.6 |

P:Propofol;
Note that aminophylline greatly reversed the effects produced by propofol as assessed by the combined scores; The reduced effect of aminophylline compared to the control (P = O, no propofol or awake(*)) values indicates aminophylline excitatory behavior; Mean values (n = 9).

EXAMPLE 3

AMINOPHYLLINE REDUCES RECOVERY TIME FROM ISOFLURANE/NITROUS OXIDE ANESTHESIA

Aminophylline has been reported to antagonize the effects of diazepam and ketamine in surgical patients. See *Lancet*, 1982 2:1467 and *Anesth Analg* 1998; 86:S480. However, it has not been studied in patients anesthetized with isoflurane, or other classes of compounds. This experimental study assessed whether aminophylline could expedite recovery of psychomotor and cognitive function in patients anesthetized with isoflurane/$N_2O$.

Methods: After institutional approval, informed consent was obtained from 20 ASA I adult patients scheduled for orthognathic surgery (sagittal splitting ramus osteotomy) under general anesthesia. This study was randomized, double-blind, and placebo controlled. Premedication was restricted to atropine (0.5 mg, IM) about 30 min prior to the operation. Anesthesia was induced with propofol (2 mg/kg, IV) and vecuronium (0.1 mg/kg, IV); after intubation, anesthesia was maintained with isoflurane/$N_2O$. The end-tidal concentration of isoflurane and $N_2O$ were continuously monitored (Capnomac Ultima™) and maintained at 0.9% and 67% respectively for at least 30 min period during spontaneous ventilation. At the end of surgery, and immediately after isoflurane and $N_2O$ were discontinued, 18 ml of a study drug solution containing either aminophylline 5 mg/kg (group A, n=10) or 0.9% saline (group S, n=10) was infused over a 3 minute period. The following variables were measured: Awakening time (opening eyes at command); squeezing investigator's hand, orientation (name, date, and birthday); cognitive function was assessed by asking the patient to perform three simple arithmetic calculations at 15, 30, 45 and 60 minutes after injection of the study solution (saline or aminophylline). Postoperative pain was measured using a visual analogue scale (VAS) at 30 and 60 min. Mann-Whitney U test, Wilcoxon rank sum test and Fisher's exact test were used for statistical significance (<0.05). Data are shown in Table 1, with mean ±SD (standard deviation)

Results and Conclusion: Recovery times in all variables measured, including psychomotor and cognitive functions, were significantly shorter in the aminophylline group as can be seen in Table 1.

TABLE 3

|  | Group S (n = 10) | Group A (n = 10) |
| --- | --- | --- |
| Anesthesia Time (min) | 175 ± 61 | 171 ± 23 |
| Emergence and Psychomotor Functions |  |  |
| Eye Opening (min) | 11.5 ± 2.7 | 6.0 ± 1.6* |
| Squeezing Hand (min) | 16.9 ± 6.1 | 9.4 ± 2.6* |
| Orientation (min) | 20.4 ± 5.6 | 13.0 ± 1.8* |
| Cognitive Function (number of patients performing arithmetic calcuations correctly) |  |  |
| Time After Injection |  |  |
| 15 min | 1 | 2 |
| 30 min | 5 | 10* |
| 45 min | 9 | 10 |
| 60 min | 10 | 10 |
| VAS Pain Score |  |  |
| Time After Injection |  |  |
| 30 min | 40.2 ± 25.4 | 41.3 ± 19.9 |
| 45 min | 51.7 ± 21.7 | 48.6 ± 15.8 |

S:Saline;
A:Aminophylline,
* Significantly different from Group S, p < 0.05

There were no significant differences in the demographic data, operation and anesthesia time between the two groups. Respiratory rate, blood pressure, EKG and heart rate showed no significant difference before and after aminophylline injection. However, the degree of postoperative pain was not significantly different between the two groups. Thus, the results indicate that aminophylline can be useful for expediting recovery from isoflurane/N20 anesthetic effects, and that this effect can be useful in all animals, such as mammals, including humans.

Therefore, as used herein, expressions, such as: accelerate anesthetic recovery, to counteract the anesthetic action, accelerate anesthesia recovery, and/or similar terms, mean to shorten, minimize, antagonize, reverse or attenuate the effects produced by the drugs used to produce anesthesia. Some of these effects include cognitive and psychomotor functions, cardiovascular, respiratory and metabolic effects.

While preferred embodiments of the invention have been illustrated and described in detail in the figures and foregoing description, the same is to be considered as illustrative and not restrictive in character. For example, the term xanthine compounds incorporates relevant (R) and (S) enantiomers and racemic mixtures thereof, and the pharmaceutically acceptable salts thereof, provided such compounds exist or can be synthesized, including all xanthine compounds disclosed in U.S. Pat. No. 5,696,124, and provided such compounds can generate a $\alpha AR$ greater than 0 when tested in accordance with the methods described herein. As used herein, the terms alkyl, alkenyl, alkynyl, alkoxy, amino, and aryl incorporate substituted derivatives thereof, such as but not limited to hydroxyalkyls, alkylaminos, and arylaminos. The term xanthine compound as used in the context of the present invention is limited hereby to cover only such compounds that can be used in accordance with the objectives of the present invention to reduce anesthesia recovery time (i.e., have a$\Delta AR$ greater than 0 using the method described herein), and/or counteract the effects of certain drugs. Thus, it is understood that only the preferred embodiments have been shown and described, and that all changes and modifications that come within the spirit of the invention are desired to be protected.

What is claimed is:

1. A method of accelerating anesthetic recovery, comprising the step of administering a sufficient amount of a pharmaceutically acceptable xanthine compound to an anesthetized patient to accelerate anesthetic recovery, wherein said anesthesia is produced in the patient with at least one compound selected from the group consisting of propofol, an inhaled anesthetic, an opioid, an etomidate, a barbiturate, and an anesthetic purine compound.

2. The method of claim 1, wherein said patient is a human.

3. The method of claim 1, wherein said xanthine compound has the structure:

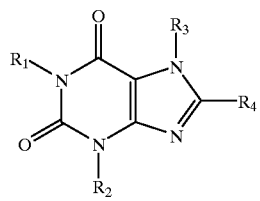

wherein $R_1$, $R_2$, $R_3$, and $R_4$ are independently selected from the group of moieties consisting of a hydrogen, an alkyl, an alkenyl, an alkynyl, an alkoxy, an amino, an aryl, a cycloalkyl, a hydroxy, a halogen, and a nitro.

4. The method of claim 1, wherein said xanthine compound has the structure:

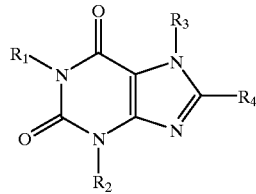

wherein $R_1$, $R_2$, $R_3$, and $R_4$ are independently selected from the group of moieties consisting of a hydrogen, an alkyl, and an aryl.

5. The method of claim 4, wherein one of $R_1$, $R_2$, and $R_3$ is H, and two of $R_1$, $R_2$, and $R_3$ are independently a $C_1$–$C_4$ alkyl.

6. The method of claim 1, wherein said xanthine compound is selected from the group consisting of 1,3-dimethyl xanthine, 3,7-dimethyl xanthine, and 1,3,7-trimethyl xanthine.

7. The method of claim 1, wherein said xanthine compound is aminophylline.

8. The method of claim 1, wherein said anesthetic recovery is characterized by recovery of at least one function selected from the group consisting of psychomotor function, cardiovascular function, and respiratory function.

9. The method of claim 1, wherein said xanthine compound is theophylline.

10. A method for accelerating anesthetic recovery comprising the step of administering a sufficient amount of a pharmaceutically acceptable xanthine compound to a patient during and/or following the production of surgical anesthesia in the patient, wherein said anesthesia is produced in the patient with at least one compound selected from the group consisting of propofol an inhaled anesthetic, an opioid, an etomidate, a barbiturate, and a purine compound, and wherein said anesthetic recovery is characterized by recovery of at least one function selected from the group consisting of psychomotor function, cardiovascular function, and respiratory function.

11. The method of claim 10, wherein said xanthine compound has the structure:

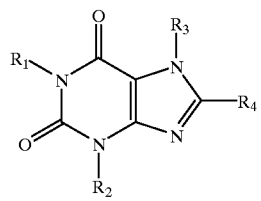

wherein $R_1$, $R_2$, $R_3$, and $R_4$ are independently selected from the group of moieties consisting of a hydrogen, an alkyl, and an aryl.

12. The method of claim 11, wherein one of $R_1$, $R_2$, and $R_3$ is H, and two of $R_1$, $R_2$, and $R_3$ are independently $C_1$–$C_4$ alkyl.

13. The method claim 10, wherein said xanthine compound is selected from the group consisting of 1,3-dimethyl xanthine, 3,7-dimethyl xanthine and 1,3,7-trimethyl xanthine.

14. The method of claim 10, wherein said patient is a human.

15. The method of claim 14, wherein said xanthine compound is aminophylline.

16. The method of claim 10, wherein said xanthine compound is theophylline.

* * * * *